US012778400B2

(12) United States Patent
Duan et al.

(10) Patent No.: US 12,778,400 B2
(45) Date of Patent: Nov. 3, 2026

(54) MEDICAL DETECTION APPARATUS AND MEASURING COMPONENT THEREOF

(71) Applicant: Ankon Medical Technologies (Shanghai) Co., LTD., Shanghai (CN)

(72) Inventors: Xiaodong Duan, Pleasanton, CA (US); Shupeng Zhang, Shanghai (CN); Lei Liu, Shanghai (CN)

(73) Assignees: ANKON MEDICAL TECHNOLOGIES (SHANGHAI) CO., LTD., Shanghai (CN); ANX IP HOLDING PTE. LTD., Singapore (SG)

(*) Notice: Subject to any disclaimer, the term of this patent is extended or adjusted under 35 U.S.C. 154(b) by 1034 days.

(21) Appl. No.: 17/910,836

(22) PCT Filed: Mar. 10, 2020

(86) PCT No.: PCT/CN2020/078529
§ 371 (c)(1),
(2) Date: Feb. 9, 2023

(87) PCT Pub. No.: WO2021/179152
PCT Pub. Date: Sep. 16, 2021

(65) Prior Publication Data

US 2024/0023845 A1 Jan. 25, 2024

(51) Int. Cl.

| | |
|---|---|
| ***A61B 1/04*** | (2006.01) |
| ***A61B 1/00*** | (2006.01) |
| ***A61B 5/00*** | (2006.01) |
| ***A61B 5/145*** | (2006.01) |
| ***A61B 5/1459*** | (2006.01) |

(52) U.S. Cl.
CPC .......... *A61B 1/044* (2022.02); *A61B 1/00181* (2013.01); *A61B 1/041* (2013.01); *A61B 5/14539* (2013.01); *A61B 5/14546* (2013.01); *A61B 5/1459* (2013.01); *A61B 5/6861* (2013.01); *A61B 1/00016* (2013.01)

(58) Field of Classification Search
CPC .............................. A61B 5/1455; A61B 1/044
See application file for complete search history.

(56) References Cited

U.S. PATENT DOCUMENTS

2002/0042065 A1* 4/2002 Han .................. A61B 5/14865 435/7.9
2005/0137468 A1 6/2005 Avron et al.
(Continued)

FOREIGN PATENT DOCUMENTS

CN 102006822 A 4/2011
CN 103096790 A 5/2013
(Continued)

*Primary Examiner* — Marjan Fardanesh
(74) *Attorney, Agent, or Firm* — Treasure IP Group, LLC

(57) ABSTRACT

A medical detection apparatus and a measuring component thereof are provided. The medical detection apparatus includes a housing and a measuring component. The measuring component is mounted on the outer wall of the housing for measuring the concentration of a parameter to be measured in the external environment of the housing. Through arrangement of the measuring component, the medical detection apparatus detects various parameters in the digestive tract, and the accuracy of detection is improved.

22 Claims, 7 Drawing Sheets

(56) References Cited

U.S. PATENT DOCUMENTS

| | | | | |
|---|---|---|---|---|
| 2013/0202499 | A1 * | 8/2013 | Gil | G01N 21/78 436/66 |
| 2020/0072756 | A1 | 3/2020 | Jabbarzadeh et al. | |

FOREIGN PATENT DOCUMENTS

| | | | |
|---|---|---|---|
| CN | 103494594 | A | 1/2014 |
| CN | 104971423 | A | 10/2015 |
| CN | 105342543 | A | 2/2016 |
| CN | 105593679 | A | 5/2016 |
| CN | 208942084 | U | 6/2019 |
| EP | 0250034 | A2 | 12/1987 |
| WO | 2009057120 | A2 | 5/2009 |

* cited by examiner

MEDICAL DETECTION APPARATUS AND MEASURING COMPONENT THEREOF

CROSS-REFERENCE OF RELATED APPLICATIONS

The application is a National Phase Application of PCT International Application No. PCT/CN2020/078529, International Filing Date Mar. 10, 2020, published Sep. 16, 2021, as International Publication Number WO 2021/179152, all of which are incorporated herein by reference in their herein.

FIELD OF INVENTION

The present invention relates to a medical device, and more particularly, to a medical detection apparatus and a measuring component thereof.

BACKGROUND

With the accelerating pace of life, people's life pressures is gradually increasing, which, coupled with changes in the structure of diet, has led to the fact that digestive tract diseases have become a type of disease that seriously affects people's quality of life. Diagnosis and treatment of the digestive tract diseases are based on accurate examination of physiological parameters and mucosal state of the digestive tract.

At present, endoscopic devices are usually used to visually observe the mucosa of digestive tract. However, due to limitations in technology integration, commercially available endoscopes are only capable of image observation of the digestive tract mucosa but incapable of obtaining other useful information in the digestive tract. Therefore, the existing endoscopes have limited functions and cannot complete accurate detection of the digestive tract.

SUMMARY OF THE INVENTION

The present invention discloses a medical detection apparatus and a measuring component thereof. The medical detection apparatus has a high detection accuracy.

According to a first aspect of the present invention, a medical detection apparatus is disclosed. The medical detection apparatus comprises:

a housing; and a measuring component, mounted on the outer wall of the housing for measuring the concentration of a parameter to be measured in the external environment of the housing.

In a possible embodiment, the measuring component comprises a polyionic gel and a dye, and the dye is filled in the polyionic gel.

When concentrations of the parameter to be measured are different, the dye changes color.

In a possible embodiment, the measuring component comprises one or more of a pH measuring component, an occult blood measuring component, a pepsin measuring component, and a trypsin measuring component.

In a possible embodiment, the dye of the pH measuring component is a pH sensitive dye which can change color in environments with different pH values.

In a possible embodiment, hydrogen ions in the external environment of the housing can enter the pH measuring component through the polyionic gel, and the hydrogen ions in the pH measuring component can enter the external environment of the housing through the polyionic gel.

The pH-sensitive dye can combine or dissociate with hydrogen ions to create a dynamic equilibrium.

In a possible embodiment, the dye of the occult blood measuring component comprises a methylene blue dye which can change color in environments with different occult blood concentrations.

In a possible embodiment, hemoglobin in the external environment of the housing can combine and react with the polyionic gel and the methylene blue dye in the occult blood measuring component.

In the presence of hemoglobin, through a redox reaction, the methylene blue dye can show color, the methylene blue dye shows different colors when the concentration of the hemoglobin is different.

In a possible embodiment, the dye of the pepsin measuring component comprises a bromophenol blue dye which can change color in environments with different pepsin concentrations.

In a possible embodiment, the pepsin in the external environment of the housing can combine with the polyionic gel and bromophenol blue dye in the pepsin measuring component.

The light scattering signal of the combined bromophenol blue dye changes to show different colors, and the color of the bromophenol blue dye is different when the concentration of pepsin is different.

In a possible embodiment, the dye of the trypsin measuring component comprises a bromophenol purple dye which can change color in environments with different trypsin concentrations.

In a possible embodiment, the trypsin in the external environment of the housing can combine with the polyionic gel and bromophenol purple dye in the trypsin measuring component.

The volume and light scattering signal of the combined bromophenol blue dye change to show different colors, and the color of the bromophenol purple dye is different when the concentration of trypsin is different. The arrangement of the measuring components on the outer wall of the housing is a partition arrangement or an alternate arrangement.

In a possible embodiment, the medical detection apparatus comprises a plurality of the measuring components.

The ranges of the measuring components are not completely the same, and/or the resolutions of the measuring components are not completely the same.

In a possible embodiment, the housing comprises a transparent portion.

The medical detection apparatus further comprises an imaging assembly. The imaging assembly is located in the inner cavity of the housing, and can observe the external environment of the housing through the transparent portion.

In a possible embodiment, the housing comprises a first end and a second end which are arranged opposite each other in the axial direction, and both the first end and the second end comprise the transparent portion.

The medical detection apparatus comprises two said imaging assemblies, and the two imaging assemblies are arranged corresponding to the two transparent portions.

The measuring component is mounted on the outer wall of the first end or the second end; or, the medical detection apparatus comprises at least a first measuring component and a second measuring component, and the first measuring component and the second measuring component have different ranges. One of the first measuring component and the second measuring component is mounted on the outer wall of the first end, and the other of the first measuring component and the second measuring component is mounted on the outer wall of the second end.

In a possible embodiment, the medical detection apparatus further comprises a data transmission assembly.

The imaging assembly comprises a lens and an image sensor, the lens and the image sensor are connected by a mechanical structure and/or glue.

The image sensor is electrically connected or connected by signal to the data transmission assembly, and the lens and the data transmission assembly are connected by a mechanical structure and/or glue.

In a possible embodiment, the lens is disposed in the inner cavity of the housing and has an effective imaging angle $\alpha 1$, and the transparent portion can cover the space where the effective imaging angle $\alpha 1$ is located.

The image sensor has a display image angle $\alpha 2$, the transparent portion can cover the space where the display image angle $\alpha 2$ is located, and $\alpha 1 > \alpha 2$.

The measuring component is mounted on the outer wall of the housing and is located in the space between the effective imaging angle $\alpha 1$ and the display image angle $\alpha 2$.

The data transmission assembly can obtain the data of the measuring component.

In a possible embodiment, the lens is disposed in the inner cavity of the housing and has an effective imaging angle $\alpha 1$, and the transparent portion can cover the space where the effective imaging angle $\alpha 1$ is located.

The image sensor has a display image angle $\alpha 2$, the transparent portion can cover the space where the display image angle $\alpha 2$ is located, and $\alpha 1 > \alpha 2$.

The measuring component is mounted on the outer wall of the housing and is located in the space that the display image angle $\alpha 2$ takes up;

The image sensor can recognize the data of the measuring component.

In a possible embodiment, the measuring component is located in the middle of the space that the display image angle $\alpha 2$ takes up.

In a possible embodiment, the measuring component is affixed to the outer wall of the housing through a transparent adhesive material.

In a possible embodiment, the measuring component is further adhered to the outer wall of the housing by an edge sealant, and the edge sealant covers the outer edge of the measuring component.

In a possible embodiment, the housing is in a capsule-shaped structure;

the medical detection apparatus is a capsule endoscope.

According to a second aspect of the present invention, a measuring component of a medical detection apparatus is disclosed. The measuring component comprises a polyionic gel and a dye, and the dye is filled in the polyionic gel;

When the concentration of the parameter to be measured is different, the dye can change color.

Therefore, in the embodiments of the present invention, through arrangement of measuring components, the medical detection apparatus can detect various parameters in the digestive tract (including pH, occult blood concentration, pepsin concentration, trypsin concentration, etc.). As a result, the detection accuracy of the apparatus in the digestive tract is improved, while the medical detection apparatus provides multiple functions, improving its practicability.

It should be understood that the above description and the details to be set forth in the following text are only exemplary, which are not intended to limit the invention.

BRIEF DESCRIPTION OF THE DRAWINGS

In order to illustrate the technical solutions of the embodiments of the present application more clearly, the accompanying drawings that need to be used in the embodiments will be briefly introduced below. Obviously, the accompanying drawings in the following description are only some embodiments of the present application, for those of ordinary skill in the art, other drawings can also be obtained based on these drawings without any creative effort.

Marks in the drawings.

1—Housing;

11—Transparent portion;

12—Upper shell;

13—Lower shell;

14—Edge sealant;

2—Data transmission assembly;

21—Data collection and processing module;

22—Antenna;

23—Battery;

3—Measuring component;

31—Body portion;

32—Adhesive material;

33—pH measuring component;

34—Occult blood measuring component;

35—Pepsin measuring component;

36—Trypsin measuring component;

4—Imaging assembly;

41—Lens;

411—Camera base;

42—Image sensor;

43—Illuminating source;

431—LED structural member;

5—IR switch;
D1—Effective imaging angle boundary;
D2—Display image angle boundary.

DETAILED DESCRIPTION

The present invention will be understood and appreciated more fully from the following detailed description taken in conjunction with the appended figures.

It should be clear that the described embodiments are only a part of the embodiments of the present invention, rather than all of the embodiments. Based on the embodiments in this invention, all other embodiments obtained by a person of ordinary skill in the art without creative work shall fall within the protection scope of this application.

The terms used in the embodiments of the present invention are only for the purpose of describing specific embodiments, and are not intended to limit the invention. The singular forms "a", "said" and "the" used in the embodiments of the present application and the appended claims are also intended to include plural forms, unless the context clearly indicates other meanings.

It should be appreciated that the term "and/or" used herein only means an association relationship describing associated objects, indicating that there can be three types of relationships. For example, A and/or B can refer to: only A exists, both A and B exist, and only B exists. In addition, the character "/" in this text generally indicates that the associated objects are in an "or" relationship.

It should be noted that the "upper", "lower", "left", "right" and other directional words set forth in the embodiments of the present invention are described from the angle shown in the accompanying figures, and should not be construed as limitations to the embodiments of the invention. Moreover, in the context, it should also be understood and appreciated that when it is mentioned that an element is connected "on" or "under" another element, it can not only be directly connected "on" or "under" the other element, but it can also indirectly connected "on" or "under" the other element through an intermediate element.

Figure 1:
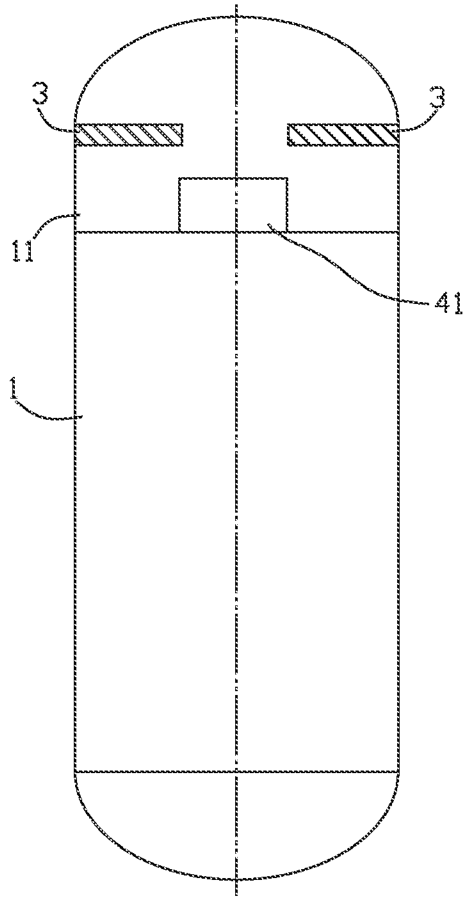
FIG. 1 is a schematic illustration of a first exemplar embodiment of a medical detection apparatus according to the aspects of the present invention.
Figure 2:
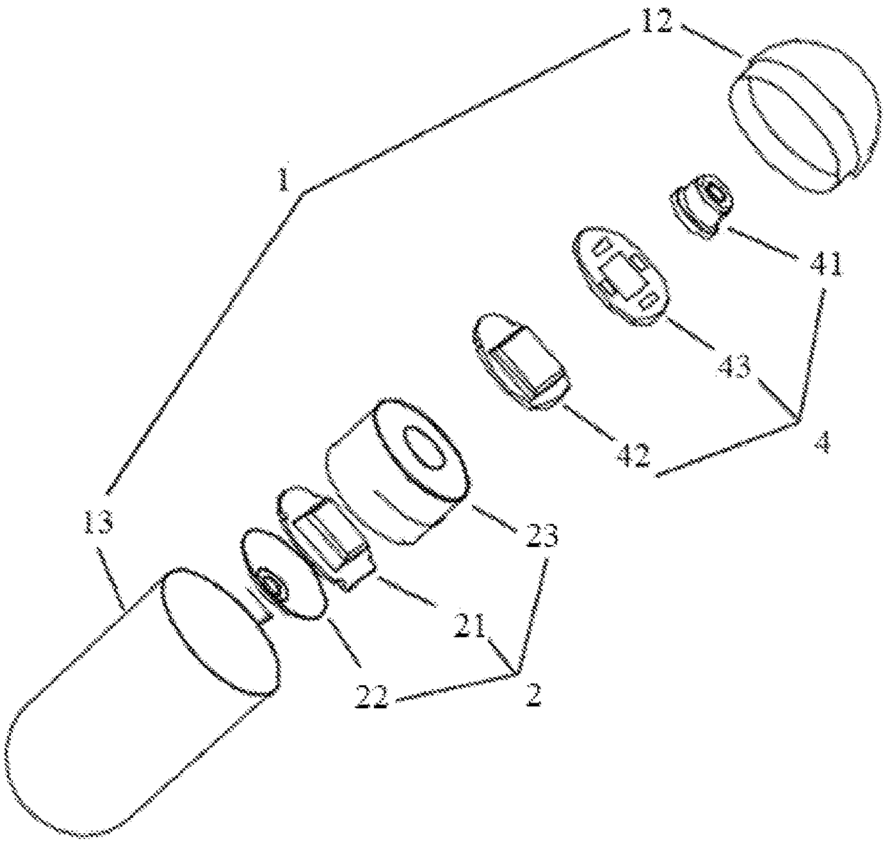
FIG. 2 is an exploded view of the medical detection apparatus of FIG. 1.

Referring to FIG. 1 and FIG. 2, a medical detection apparatus is disclosed. The apparatus comprises a housing 1 and a measuring component 3, wherein the housing 1 further comprises an upper shell 12 and a lower shell 13 which are fixedly connected to form an inner cavity of the housing 1. The measuring component 3 is mounted on the outer wall of the housing 1 for measuring the parameters of the external environment of the housing 1. When the medical detection apparatus is used for digestive tract detection, it can detect the pH value, occult blood concentration, pepsin concentration, trypsin concentration and other parameters of the digestive tract.

Therefore, in the embodiments of the present invention, through arrangement of measuring components, the medical detection apparatus can detect various parameters in the digestive tract (including pH, occult blood concentration, pepsin concentration, trypsin concentration, etc.). As a result, the detection accuracy of the medical detection apparatus in the digestive tract is improved.

Specifically, the measuring component 3 in the embodiments of the present invention may comprise one or more of a pH measuring component 33, an occult blood measuring component 34, a pepsin measuring component 35 and a trypsin measuring component 36. The pH measuring component 33 can be used for measuring the pH of the external environment (digestive tract, for example) of the housing 1. The occult blood measuring component 34 can be used for determining whether there is occult blood and measuring the concentration of occult blood in the external environment (digestive tract, for example) of the housing 1. The pepsin measuring component 35 can be used for measuring the concentration of pepsin in the external environment of the housing 1 (digestive tract, for example). The trypsin measuring component 36 can be used for measuring the concentration of trypsin in the external environment of the housing 1 (digestive tract, for example).

Therefore, an arrangement of the measuring components 3 described above enables measuring various parameters of the digestive tract, and thereby improves the accuracy of detection results of the medical detection apparatus.

It should be noted that the medical detection apparatus in the embodiments of the present invention does not necessarily comprise the four measuring components 3, but may include only one of them or any combination thereof.

Figure 4:
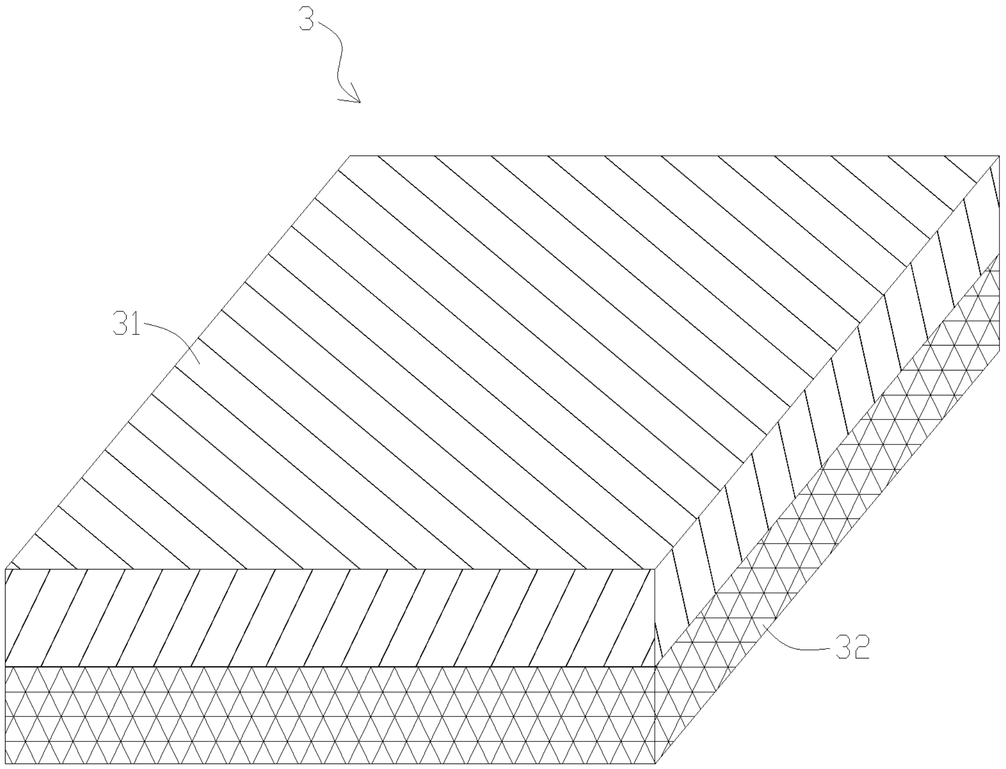
FIG. 4 shows a structure of a measuring component of the medical detection apparatus in FIG. 1.

Specifically, as shown in FIG. 4, the measuring component 3 may comprise a body portion 31 and an adhesive material 32. The adhesive material 32 is a transparent adhesive and biocompatible, so that the body portion 31 of the measuring component 3 can be affixed to the housing 1 of the medical detection apparatus through the adhesive material 32. The adhesive material 32 may be a transparent backing and is affixed to the transparent portion 11 of the housing 1. The transparent adhesive backing can be, but is not limited to, a medical grade UV adhesive, a medical instant adhesive, or a medical backing.

Figure 5:
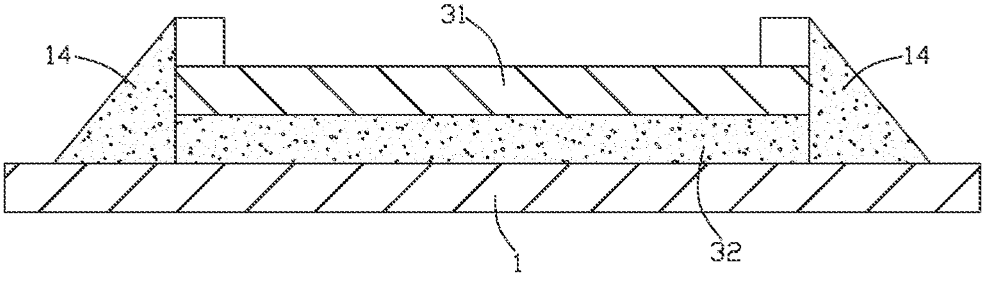
FIG. 5 shows a structure of connection between the measuring component in FIG. 4 and a housing of the medical detection apparatus.

More specifically, as shown in FIG. 5, the body portion 31 of the measuring component 3 is also connected to the outer wall of the housing 1 by an edge sealant 14. The edge sealant 14 is applied on the outer edge of the body portion 31, so that the measuring component 3 is adhered to the housing 1 by the edge sealant 14. The edge sealant 1 can be, but is not limited to, a medical grade UV adhesive, a medical instant adhesive, or a medical backing.

In this embodiment, when the outer edge of the measuring component 3 is connected to the housing 1 by the edge sealant 14, the reliability of connection between the measuring component 3 and the housing 1 can be further improved, and the risk of the measuring component 3 falling off from the housing 1 during use and installation is reduced.

Specifically, the measuring component 3 may comprise a polyionic gel and a dye, and the dye can change color. The measuring component 3 may be a thin film structure, with any shape such as a circle, a square, a polygon, etc. The specific shape of the measuring component 3 is not limited in this invention.

In a possible embodiment, the body portion 31 of the measuring component 3 comprises a polyionic gel and a dye, wherein the dye can change color, the polyionic gel is a solid substance formed by cross-linking polymerization of polymers, and the dye is filled in the polyionic gel. Due to a strong ionic interaction between the polyionic gel and the dye, the dye can be kept in the polyionic gel.

The polyionic gel contains an ion-exchange membrane structure. The ion-exchange membrane is a kind of polymer membrane that contains ion groups and has selective permeability to ions in a solution. When the measuring component 3 is in a solution environment (human digestive tract, for example), the ions (such as hydrogen ions) of a substance to be measured in the solution can enter the polyionic gel and combine with the dye in the polyionic gel to make the dye change color. In addition, in the measuring component 3, the concentration of the ions (hydrogen ions, for example) of the substance to be measured in the solution is the same as that of the ions (hydrogen ions, for example) of the substance to be measured in the polyionic gel. When the concentration of the ions (hydrogen ions, for example) of the substance to be measured in the solution increases, the ions may diffuse into the polyionic gel, thereby increasing the concentration of ions (hydrogen ions, for example) of the substance to be measured combined with the dye, which corresponds to the concentration of the substance to be measured (for example, the concentration of hydrogen ions, i.e. the pH value of the solution). When the concentration of the ions (hydrogen ions, for example) of the substance to be measured in the solution decreases, the ions (hydrogen ions, for example) of the substance to be measured in the polyionic gel may diffuse into the solution, thereby reducing the concentration of the ions (hydrogen ions, for example) of the substance to be measured combined with the dye, which corresponds to another concentration of the substance to be measured (for example, the concentration of hydrogen ions, i.e. the pH value of the solution).

Therefore, in this embodiment, the dye in the measuring component 3 can combine or dissociate with the ions (hydrogen ions, for example) of the substance to be measured to form a dynamic equilibrium, and enable a continuous measurement of the concentration of the substance to be measured.

Based on this, in this embodiment, the measuring component 3 comprising polyionic gel and dye can be easily integrated (affixed, for example) with the medical detection apparatus (a capsule endoscope, for example), and is compatible with the hardware of the medical detection apparatus after integration. A secondary packaging is not needed. Only needed is a modification of relevant software to perform pH measurement while in the process of an endoscopy in order to improve the accuracy of detection. Also, by adding a polyionic gel, while the ions of the substance to be measured in the solution can pass through the polyionic gel and combine with the dye, and the ions of the substance to be measured combined with the dye can also pass through the polyionic gel, a dynamic equilibrium between the measuring component 3 and the ions of the substance to be measured can be created, so as to realize a continuous measurement of the concentration of the substance to be measured. In addition, the measuring component 3 also contributes to industrialization to reduce cost.

In a specific embodiment, when the medical detection apparatus is used to measure the pH value of the digestive tract, the measuring component 3 comprises at least a pH measuring component 33, and the body portion 31 of the pH measuring component 33 may comprise a polyionic gel and a pH-sensitive dye, wherein the pH-sensitive dye has a different color when the concentration of hydrogen ions in the solution are different.

In the field of medical devices, pH inside the human body is mainly measured by two methods in prior art. One is using a pH electrode. The pH electrode can be made of a material sensitive to hydrogen ions, and based on electrochemistry, it can directly measure the pH of the environment to be measured with high accuracy. For example, an antimony electrode. The other is to determine the pH of the environment to be measured by color changes, with low accuracy. For example, traditional pH test papers and pH indicators.

When measuring the pH by an electrochemical method, sensors are complicated, that is, a reference electrode and a test electrode need to be packaged together, while an ion channel between the packaged electrodes and the measured environment should be ensured. For conventional use scenarios, glass electrodes, antimony electrodes, and hydrogen ion-sensitive field effect transistors ($H^{+}$SFET) can all meet the requirements. However, for a pH measurement in the human digestive tract, it is extremely difficult to integrate said pH electrodes into the capsule endoscope, which is hard to implement. In addition, if the antimony electrode is used as the pH electrode, potential biological toxicity exists.

The method of measuring pH by color change has a long history, but this method cannot continuously measure different pH environments, and it cannot be integrated into a capsule endoscope for continuous pH measurement either.

For the above reasons, in the field of medical devices, there is currently no technique that can integrate an endoscope with a traditional pH measurement sensor, or, with the current technique, the device formed by integrating an endoscope with a traditional pH measurement sensor is less reliable and the cost of integration is high.

In this embodiment, the medical detection apparatus can obtain the pH information of the digestive tract. The medical detection apparatus is integrated with the pH measuring component 33. By using the structure of the pH measuring component 33, the integration process can be simplified, and the integration cost can be reduced. The measuring component 33 comprising the polyionic gel and the dye can be easily integrated (affixed, for example) with the medical detection apparatus (a capsule endoscope, for example) without using an electrochemical electrode, and is compatible with the hardware of the medical detection apparatus after integration. A secondary packaging is not needed. Only needed is a modification of relevant software to perform pH measurement while in the process of an endoscopy in order to improve the accuracy of detection. In addition, by adding the polyionic gel, while the hydrogen ions in the solution can pass through the polyionic gel and combine with the pH-sensitive dye, and the hydrogen ions combined with the pH-sensitive dye can also pass through the polyionic gel, a dynamic equilibrium can be created between the pH measuring component 33 and the hydrogen ions, so as to realize a continuous pH measurement. In addition to measuring the pH of stomach, the pH measuring component 33 can also measure the pH of oral cavity, intestinal tract and other organs, and can show different colors according to the pH of each organ. The pH measuring component 33 also contributes to industrialization to reduce cost.

Specifically, by changing the amount or type of the pH sensitive dye in the pH measuring component 33, the range and accuracy of the pH measuring component 33 can be changed. For example, one pH measuring component 33 can meet the need for measurement of a pH of 1, 5, 7 and 8, and another pH measuring component 33 can meet the need for measurement of a pH of 2, 3, 4 and 6. Therefore, when a measuring component comprises the two pH measuring components 33, a pH measurement in the range of 1 to 8 can be satisfied, with a pH value resolution of 0.5 to 1. The difference between the above two pH measuring components 33 is that the two have different types of pH-sensitive dyes, and the two can have the same polyionic gel.

In another embodiment, when the medical detection apparatus is used to detect the existence of occult blood in the digestive tract and measure the concentration of occult blood, the measuring component 3 comprises at least an occult blood measuring component 34. The body portion 31 of the occult blood measuring component 34 may comprises a polyionic gel and a methylene blue dye, wherein the methylene blue dye shows a different color when the concentration of hemoglobin in the solution is different.

In the field of medical devices, there are two mainstream methods for detection of occult blood in digestive tract. The first one is an occult blood bead method. The basic principle of the method is to swallow a capsule-shaped device gripped by a tether, pull the capsule-shaped device out by the tether after absorbing gastric fluid at its tail, drip a color developing agent onto the capsule-shaped device, and observe the color change to determine whether there is occult blood. The second method is to detect the occult blood condition of the digestive tract by detecting the bleeding in stool with occult blood test paper.

The first method is only applicable to the detection of occult blood in the upper gastrointestinal tract, and it is an invasive test. The detection process can cause discomfort such as vomiting. The second method is only applicable to the detection of occult blood in the lower gastrointestinal tract, especially the colon and the rectum, and it is susceptible to interference such as hemorrhoids that may cause a false positive in the detection.

In this embodiment, when the occult blood measuring component 34 comprising the polyionic gel and the methylene blue dye is used, due to a strong ionic interaction between the polyionic gel and methylene blue dye, the methylene blue dye can remain in the polyionic gel without leakage. The methylene blue dye is a biological stain, which has an oxidization effect on hemoglobin. During the reaction, the methylene blue dye, after reduced by hemoglobin, turns from blue to colorless, and according to different hemoglobin concentrations, the shade of blue is different, so that the occult blood can be quantitatively detected through color change.

In this embodiment, the methylene blue dye is a kind of non-toxic dye which is blue as oxidized, and becomes colorless after reduced. In an environment of high concentration of hemoglobin, due to the metabolism of cells, the cells have strong reducing ability. Under the action of glucose-6-phosphate dehydrogenase, the methylene blue dye can be changed from blue oxidized type to colorless or light yellow reduced type. In an environment of low concentration of hemoglobin, the cells have no or quite low reducing ability, and at this point the methylene blue dye is blue or light blue. Therefore, when the methylene blue dye is blue or light blue, it means that the concentration of hemoglobin in the environment (digestive tract, for example) is low, and when the methylene blue dye is colorless or light yellow, it means that the concentration of hemoglobin in the environment (digestive tract, for example) is high.

In addition, the occult blood measuring component 34 in this embodiment enables continuous measurement and can measure the concentration of occult blood in different organs, for example, in the stomach and intestine.

Therefore, the medical detection apparatus in the embodiments of the present invention is integrated with an occult blood measuring component 34. By using the structure of the occult blood measuring component 34, the integration technique can be simplified and the cost can be reduced. More importantly, the medical detection apparatus can realize non-invasive detection with high measurement accuracy.

In still another embodiment, when the medical detection apparatus is used to measure the concentration of pepsin in the digestive tract, the measuring component 3 comprises at least a pepsin measuring component 35. The body portion 31 of the pepsin measuring component 35 may include a polyionic gel and a bromophenol blue dye, wherein the bromophenol blue dye shows a different color when the concentration of pepsin in the solution (in the digestive tract, for example) is different.

Pepsin in human gastric juice has become a biological sign of gastritis and gastric cancer. In the event of intestinal metaplasia, dysplasia and gastric cancer, the secretion of pepsin decreases. When infected with helicobacter pylori or with gastric ulcer, duodenal ulcer and other diseases, the value of pepsin increases. A large number of statistical analyses have now shown that changes in serum pepsinogen levels are associated with gastric diseases, and the detection of serum pepsinogen is considered to have an important role in the early diagnosis of gastric cancer.

In prior art, three methods are available and mainly used to detect the content of pepsin. The first method is an in vitro detection by serum collection. This method is to collect a sample in a subject and test in vitro, so as to analyze the specific content of pepsin. Therefore, the result is obtained in a single test, which has limitations for real-time monitoring of content of pepsin in gastric juice. Moreover, pepsin only works in an acidic environment and loses its activity when pH is greater than 6. Thus, the test is susceptible to the in vitro environment which may cause an inaccurate test result. The second method is to rely on a gastroscopy to confirm the diagnosis. Gastroscopy is painful, expensive, and subject to the level of doctors, and has low patient acceptance. The third method is to detect the content of pepsin using a chemiluminescent immunoassay kit. The kit includes a pepsin antigen calibrator, a sample collection solution, a sample diluent, a pepsin antibody-coated microwell plate, a pepsin antibody marker, a chemiluminescence substrate solution and a concentrated washing solution. The kit can detect the content of pepsin in gastric juice, esophageal contents, and throat secretions, and identify whether there is gastroesophageal reflux according to the detection of pepsin, and determine the effect of treatment of gastric lesions and changes in their condition according to the content of pepsin. Although this method can perform pepsin detection, it is a complex process that requires a high level of operator and testing equipment, as well as being not cost effective.

In the embodiments of the present invention, when the pepsin measuring component 35 comprising the polyionic gel and the bromophenol blue dye is used, a strong ionic interaction between the polyionic gel and the bromophenol blue dye, the dye can be kept in the polyionic gel without leakage. The bromophenol blue dye is a biological stain. Under different pH conditions, the bromophenol blue dye combines with pepsin in non-covalent bonds, and the hydrophobic nucleus of pepsin combines with the non-polar group of bromophenol blue dye. The combined aggregate has a volume larger than that of the bromophenol blue dye itself, so that the combined molar absorption coefficient and light scattering signal of the dye change, thus showing different colors. The signal intensity of the dye is proportional to the number of particles in unit volume, that is, the concentration of pepsin, so that the concentration of pepsin can be detected. During a detection, the bromophenol blue dye in the pepsin measuring component 35 shows different colors for different concentrations of pepsin, so the concentration can be quantitatively detected through color change.

In addition, since pepsin can only exist in an acidic environment, and will lose its activity in a neutral or alkaline environment, pepsin only exists in the stomach. Based on this, the pepsin measuring component 35 can only be used to measure the concentration of pepsin in the stomach, not suitable for other organs (because pepsin in other organs is inactivated). During a detection, the pepsin in the stomach combines with the bromophenol blue dye and changes the molar absorption coefficient and light scattering signal of the dye. Then, the dye shows a color. The color is proportional to the concentration of pepsin. Therefore, the corresponding protein can be detected. The pepsin measuring component 35 has different color changes in the range of low concentration to high concentration in an acidic environment, and can realize a certain continuous detection. When the environment changes (from stomach to duodenum, for example), continuous detection is not available.

Therefore, the medical detection apparatus in the embodiments of the present invention is integrated with a pepsin measuring component 35. By using the structure of the pepsin measuring component 35, the integration technique can be simplified and the cost can be reduced. More importantly, the medical detection apparatus can realize non-invasive detection with high measurement accuracy.

In yet another embodiment, when the medical detection apparatus is used to measure the concentration of trypsin in the digestive tract, the measuring component 3 comprises at least a trypsin measuring component 36. The body portion 31 of the trypsin measuring component 36 may include a polyionic gel and a bromocresol purple dye, wherein the bromocresol purple dye shows a different color when the concentration of trypsin in the solution (in the digestive tract, for example) is different.

In the embodiments of the present invention, when the trypsin measuring component 36 comprising the polyionic gel and the bromocresol purple dye is used, a strong ionic interaction between the polyionic gel and the bromocresol purple dye, the dye can be kept in the polyionic gel without leakage. The bromocresol purple dye is a biological stain. Under different pH conditions, the bromocresol purple dye combines with trypsin in non-covalent bonds and the hydrophobic nucleus of trypsin combines with the non-polar group of bromocresol purple dye. The combined aggregate has a volume larger than that of the bromocresol purple dye itself, so that the molar absorption coefficient and light scattering signal change, thus showing different colors. The signal intensity of the dye is proportional to the number of particles in unit volume, that is, the concentration of trypsin, so that the concentration of trypsin can be detected. During a detection, the bromocresol purple dye in the trypsin measuring component 36 shows different colors for different concentrations of trypsin, so the concentration can be quantitatively detected through color change.

In addition, since trypsin can only exist in a weak alkaline environment, and will lose its activity in an acidic environment, trypsin exists in pancreas and the trypsin in the pancreas can flow into the duodenum with pancreatic juice. Based on this, the trypsin measuring component 36 can only be used to measure the concentration of trypsin in the pancreas and duodenum, not suitable for other organs (because trypsin in other organs is inactivated). During a detection, the trypsin combines with the bromocresol purple dye and changes the molar absorption coefficient and light scattering signal of the dye. Then, the dye shows a color. The color is proportional to the concentration of trypsin. Therefore, the corresponding protein can be detected. The trypsin measuring component 36 has different color changes in the range of low concentration to high concentration in a weak alkaline environment, and can realize continuous detection. When the environment changes (from duodenum to jejunum, for example), continuous detection is not available.

Therefore, the medical detection apparatus in the embodiments of the present invention is integrated with a trypsin measuring component 36. By using the structure of the trypsin measuring component 36, the integration technique can be simplified and the cost can be reduced. More importantly, the medical detection apparatus can realize non-invasive detection with high measurement accuracy.

In an embodiment, the medical detection apparatus may comprise a plurality of measuring components 3, and the range of each measuring component 3 are not completely the same, and/or the resolution of each measuring component 3 are not completely the same. A combination of a plurality of measuring components 3 can meet the need for measurement of the concentrations of a variety of parameters to be measured, and improve the accuracy and range of measurement. Also, when a plurality of measuring components 3 are provided, being unable to measure the parameters to be measured or inaccurate measurement result caused by a failure of a single measuring component 3 can be avoided. For example, the medical detection apparatus may comprise a plurality of pH measuring components 33, and the range of each pH measuring component 33 are not completely the same and/or the resolution of each pH measuring component 33 are not completely the same. A combination of a plurality of pH measuring components 33 can meet the need for measurement of a range of pH, and improve the accuracy and range of measurement, and can also avoid being unable to measure the pH information or inaccurate measurement result caused by a failure of a single pH measuring component 33.

Figure 6:
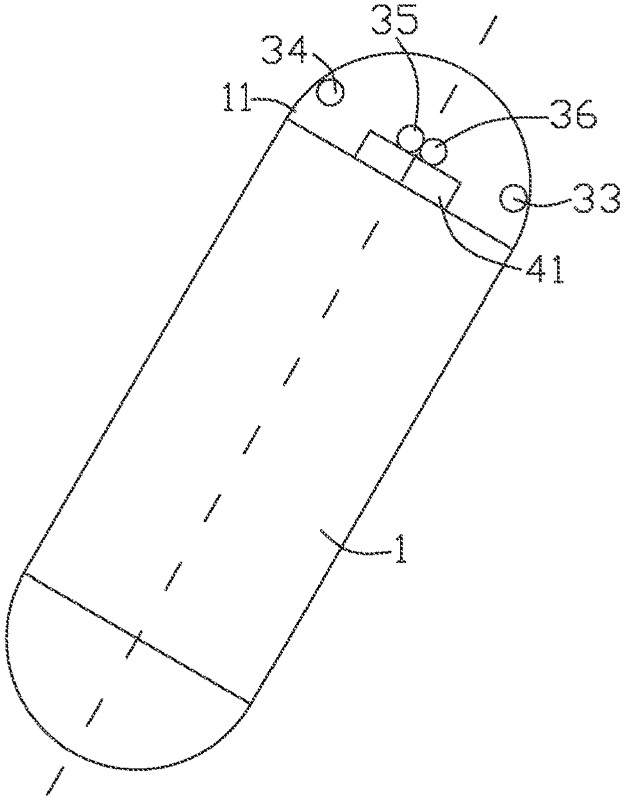
FIG. 6 is a schematic illustration of a second exemplar embodiment of the medical detection apparatus according to the aspects of the present invention.

Alternatively, the plurality of measuring components 3 may be of the same type, or different types, that is, they can be a combination of multiple types of measuring components 3. For example, in the embodiment as shown in FIG. 6, the medical detection apparatus comprises a pH measuring component 33, an occult blood measuring component 34, a pepsin measuring component 35, and a trypsin measuring component 36, so that the apparatus can be used for measurement of pH value, occult blood concentration, pepsin concentration and trypsin concentration of the digestive tract. Alternatively, each of the above pH measuring component 33, occult blood measuring component 34, pepsin measuring component 35 and trypsin measuring component 36 may comprise one or more in order to improve the accuracy of measurement. The shape of each of the above measuring components 3 can be circular.

Figure 7:
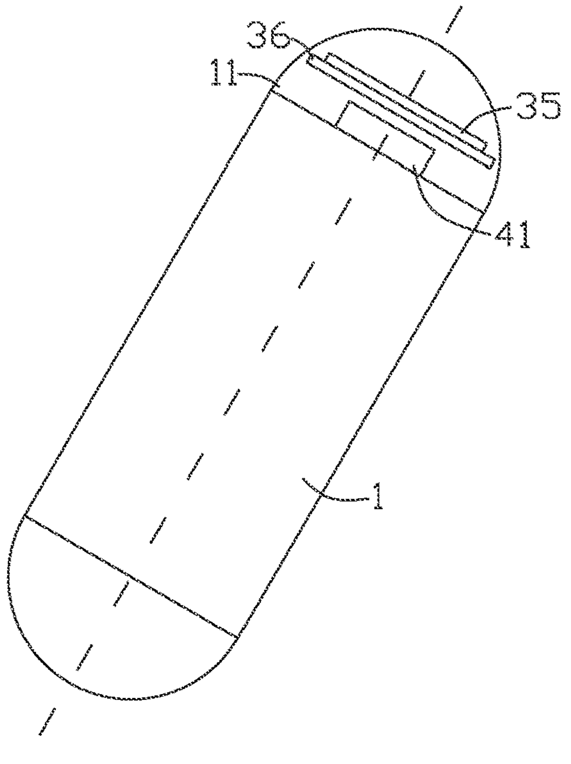
FIG. 7 is a schematic illustration of a third exemplar embodiment of the medical detection apparatus according to the aspects of the present invention.

In the embodiment as shown in FIG. 7, the medical detection apparatus comprises the pepsin measuring component 35 and the trypsin measuring component 36, so that the apparatus can be used for measurement of pepsin concentration and trypsin concentration. Alternatively, each of the above pepsin measuring component 35 and trypsin measuring component 36 may comprise one or more in order to improve the accuracy of measurement. The shape of each of the above measuring components 3 can be rectangular.

Figure 8:
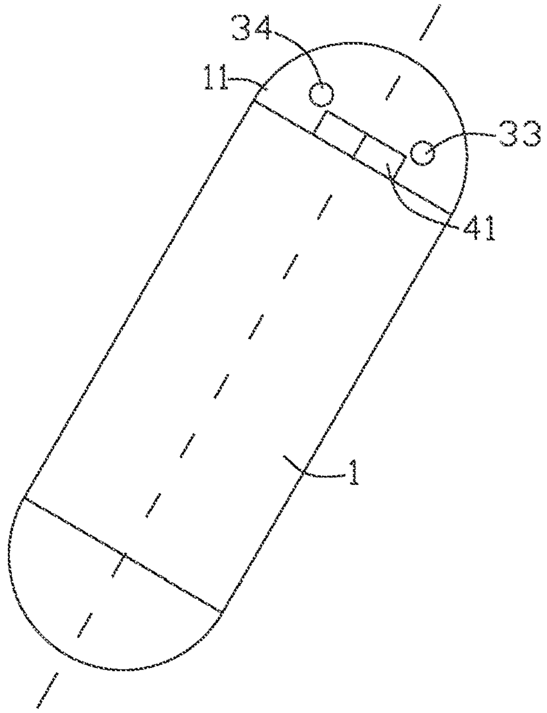
FIG. 8 is a schematic illustration of a fourth exemplar embodiment of the medical detection apparatus according to the aspects of the present invention.

In the embodiment as shown in FIG. 8, the medical detection apparatus comprises the pH measuring component 33 and the occult blood measuring component 34, so that the apparatus can be used for measurement of pH value and occult blood concentration. Alternatively, each of the above pH measuring component 33 and occult blood measuring component 34 may comprise one or more in order to improve the accuracy of measurement. The shape of each of the above measuring components 3 can be circular.

In the above embodiments, as shown in FIG. 1, the housing 1 of the medical detection apparatus comprises at least a transparent portion 11. The transparent portion 11 is made of a biocompatible transparent material, that is, through the transparent portion 11, the environment outside the housing 1 can be observed from the inside of the housing 1.

Figure 3:
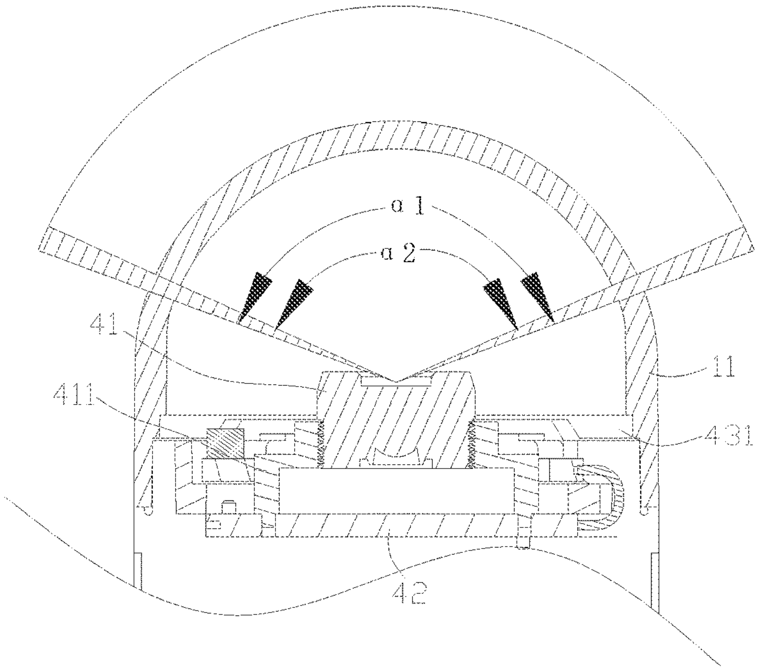
FIG. 3 is a partial section view of the medical detection apparatus of FIG. 1.

The medical detection apparatus further comprises an imaging assembly 4. As shown in FIG. 1~FIG. 3, the imaging assembly 4 is located in the inner cavity of the housing 1, and specifically comprises a lens 41, an image sensor 42 and an illuminating source 43. The lens 41 can receive light from the external environment of the housing 1 (such as human digestive tract) through the transparent portion 11 of the housing 1. The image sensor 42 is used to convert the light signal received by the lens 41 into an electrical signal. The illuminating source 43 is used for illuminating, which may be LEDs, and the illuminating source 43 comprises an LED structural member 431. Therefore, the imaging assembly 4 can take images of the external environment of the housing 1 based on the principle of optical imaging. Based on this, the medical detection apparatus in the embodiments of the present invention may be an endoscope.

Further, as shown in FIG. 2 and FIG. 3, the medical detection apparatus comprises a data transmission assembly 2, which is located in the inner cavity of the housing 1, and specifically comprises a data collection and processing module 21, an antenna 22, and one or more batteries 23. The batteries 23 provide power for components in the imaging assembly 4 and the data transmission assembly 2. The data collection and processing module 21 is electrically connected or connected by signal to the imaging assembly 4, so as to be able to identify and process the information in the imaging assembly 4. The antenna 22 is used to transmit the obtained information to an external receiver.

Specifically, the medical detection apparatus may be a capsule endoscope. When assembling, the circuit board of the capsule endoscope is first connected to the imaging assembly 4 and the data transmission assembly 2, wherein each assemblies is mainly connected by UV glue, to construct a capsule core with camera function, and then the capsule core put into the housing 1. The capsule core is first put into the lower shell 13, and then the upper shell 12 is mounted. The LED structural member 431 is snapped in between the upper shell 12 and the lower shell 13, so that the LED structural member 431 is fixed in place in the capsule endoscope, and the capsule core is fixed inside the housing 1.

Therefore, when the medical detection apparatus is in a certain region in human body, its measuring component 3 can show different colors according to concentrations of the parameters to be measured. The concentrations of the parameters to be measured can be quantitatively detected by color changes. The color changes can be identified by obtaining an image of the measuring component 3 through the lens 41 of the imaging assembly 4. The color information is transmitted to an external receiver via the data transmission assembly 2 and can be displayed in real time, thus facilitating the detection. Further, the medical detection apparatus can also take images of the external environment thereof through the lens 41 of the imaging assembly 4. The image information can be transmitted to an external receiver via the data transmission assembly 2 and can be displayed in real time. Accordingly, the health condition of the region can be determined.

In the embodiments of the present application invention, the medical detection apparatus can observe the health state of mucosa in digestive tract by an arrangement of the imaging assembly 4 and the data transmission assembly 2, and can measure the concentrations of the parameters to be measured in the digestive tract by an arrangement of the measuring component 3. That is, the medical detection apparatus integrates an endoscope device and the measuring component 3. Also, by changing the structure and type of the measuring component 3, the process of integrating the two components set forth can be simplified and the integration cost can be reduced.

Specifically, as shown in FIG. 3, the lens 41 is installed in the inner cavity of the housing 1. The lens 41 has an effective imaging angle $\alpha$1, and the transparent portion 11 of the housing 1 can cover the space where the effective imaging angle $\alpha$1 is located. Therefore, The field of view of the lens 41 is not blocked. In addition, as shown in FIG. 3, the image sensor 42 has a display image angle $\alpha$2, and the transparent portion 11 of the housing 1 can also cover the space where the display image angle $\alpha$2 is located. Therefore, the imaging area of the image sensor 42 is not blocked.

After the lens 41 and the image sensor 42 are installed, $\alpha$1 is greater than $\alpha$2. That is to say, although the lens 41 can take images in the range corresponding to $\alpha$1, and the corresponding range of $\alpha$1 has an effective imaging angle boundary D1, the range in which the image sensor 42 can display the images is the range corresponding to $\alpha$2, and the range corresponding to $\alpha$2 has a display image angle boundary D2. For example, the effective imaging angle $\alpha$1 may be 140°, and the display image angle $\alpha$2 may be 135°.

Figure 10:
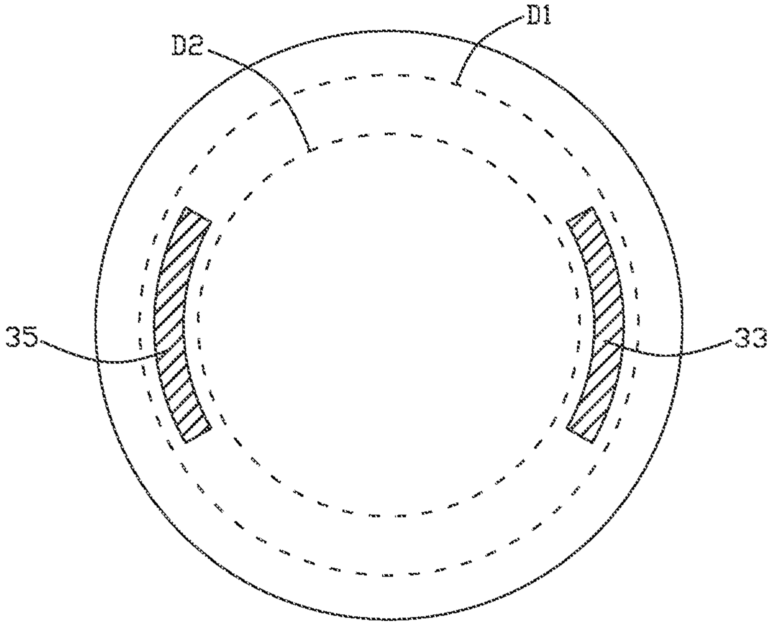
FIG. 10 is a schematic illustration of a sixth exemplar embodiment of the medical detection apparatus, in a top view, according to the aspects of the present invention.

Based on this, in the first embodiment, as shown in FIG. 10, the measuring component 3 is mounted on the transparent portion 11 and is located in the space between the effective imaging angle $\alpha$1 and the display image angle $\alpha$2. That is, the measuring component 3 is located between the effective imaging angle boundary D1 and the display image angle boundary D2. A plurality of measuring components 3 can be arranged between the effective imaging angle boundary D1 and the display image angle boundary D2, and the plurality of measuring components 3 may be of the same type or different types. In the embodiment shown in FIG. 10, for example, there is a pH measuring component 33 and a pepsin measuring component 35 between the effective imaging angle boundary D1 and the display image angle boundary D2, and both of them may be of an arc-shaped structure.

At this point, in the viewing area of the image sensor 42, the conditions of the measuring component 3 cannot be observed, but the measuring component 3 is located within the imaging range of the lens 41. Therefore, the lens 41 and the data transmission assembly 2 can read the color of the measuring component 3 and can transmit the color information to the external receiver via the antenna 22. The color information is shown on the external receiver and based on the color information, the concentration of the parameter to be measured is obtained. Since the measuring component 3 does not occupy the imaging area of the image sensor 42, a complete image of the mucosa of digestive tract can be observed. The image can be transmitted to the external receiver via the antenna 22, and displayed on the external receiver to observe the health condition of the digestive tract.

Figure 11:
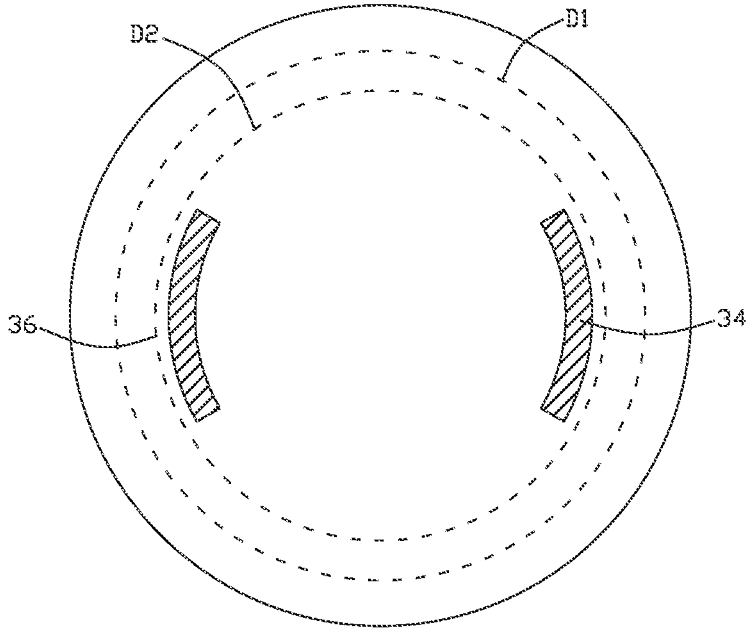
FIG. 11 is a schematic illustration of a seventh exemplar embodiment of the medical detection apparatus, in a top view, according to the aspects of the present invention.

In another embodiment, as shown in FIG. 11, the measuring component 3 is mounted on the transparent portion 11 and is located in the space occupied by the display image angle $\alpha$2. That is, the measuring component 3 is located within and close to the display image angle boundary D2, so that the measuring component 3 occupying the middle position of the display image range can be avoided, thus reducing the blocking out of image by the measuring component 3. At this point, the measuring component 3 is located in the imaging area of the image sensor 42. The image sensor 42 transmits the color information of the measuring component 3 to the external receiver, to enable a user to observe the measuring component 3 displayed by color, and the color information can also be transmitted to the external receiver via the antenna 22, so that the concentration of the parameter to be measured is displayed on the external receiver. Therefore, the medical detection apparatus in this embodiment can collect the concentration of the parameter to be measured in the digestive tract while observing the mucosa of the digestive tract.

One or more measuring components 3 can be arranged within the display image angle boundary D2 of the medical detection apparatus, and the measuring components 3 may be of the same type or different types. In the embodiment shown in FIG. 11, an occult blood measuring component 34 and a trypsin measuring component 36 are arranged within the display image angle boundary D2, and both of them may be of an arc-shaped structure and close to the display image angle boundary D2.

In still another embodiment, the measuring component 3 is mounted on the transparent portion 11 and is located in the space occupied by the display image angle α2. That is, the measuring component 3 is located within the display image angle boundary D2, and specifically, the measuring component 3 may be located in the middle of the space occupied by the display image angle α2.

At this point, the measuring component 3 is located in the imaging area of the image sensor 42. The image sensor 42 transmits the color information of the measuring component 3 to the external receiver, to enable a user to observe the measuring component 3 displayed by color, and the color information can also be transmitted to the external receiver via the antenna 22, so that the concentration of the parameter to be measured is displayed on the external receiver. Therefore, the medical detection apparatus in this embodiment can collect the concentration of the parameter to be measured in the digestive tract while observing the mucosa of the digestive tract. When the measuring component 3 is located in the middle of the space occupied by the display image angle α2, it is easy to be observed by a user with reduced blockage, so that the more accurate concentration of the parameter to be measured can be obtained.

The medical detection apparatus may comprise one or more measuring components 3, and the measuring components 3 may be of the same type or different types. In the embodiment shown in FIG. 12, a plurality of pepsin measuring components 35 and trypsin measuring components 36 are arranged between the display image angle boundary D2 and the effective imaging angle boundary D1, and the pepsin measuring components 35 and trypsin measuring components 36 are all located in the corner of the field of view. A pH measuring component 33 is arranged within the display image angle boundary D2, and the pH measuring component 33 is located in the middle of the space occupied by the display image angle α2. All of the measuring components 3 can be designed to be circular.

Figure 12:
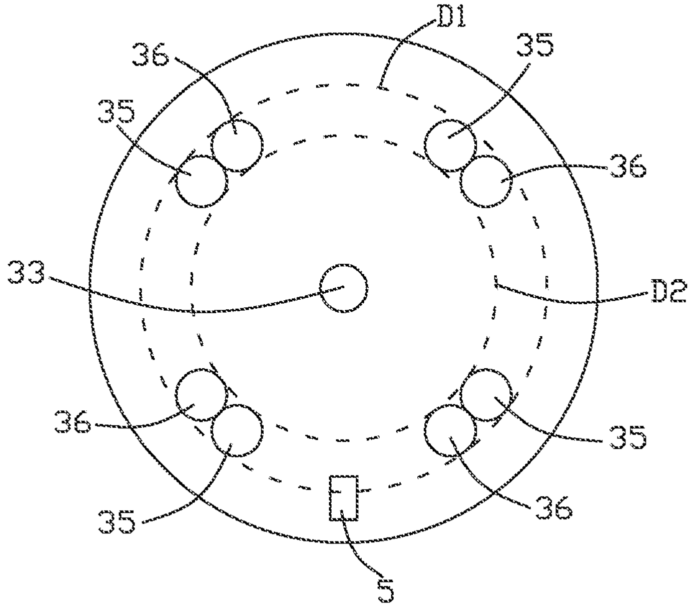
FIG. 12 is a schematic illustration of an eighth exemplar embodiment of the medical detection apparatus, in a top view, according to the aspects of the present invention.

As shown in FIG. 12, the medical detection apparatus may further comprise an infrared switch 5, which can function to turn on the measuring components 3, so that the measuring components 3 of the medical detection apparatus can start working.

Figure 13:
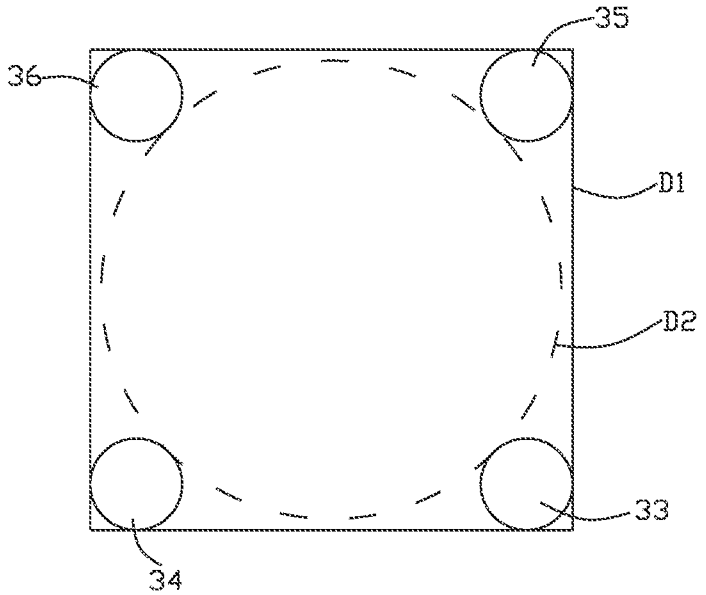
FIG. 13 is a schematic illustration of a ninth exemplar embodiment of the medical detection apparatus, in a top view, according to the aspects of the present invention.

In the embodiments shown in FIGS. 10 to 12, both the effective imaging angle boundary D1 of the lens 41 and the display image angle boundary D2 in the imaging assembly 4 can be circular, and the two are concentric. In the embodiment as shown in FIG. 13, the effective imaging angle boundary D1 of the lens 41 of the imaging assembly 4 may be a square, and the image angle boundary D2 may be a circle. Then, when the measuring components 3 are located between the display image angle boundary D2 and the effective imaging angle boundary D1, they can be at the four corners of the effective imaging angle boundary D1.

In an embodiment, the arrangement of the measuring components 3 on the outer wall of the housing 1 is a partition arrangement or an alternate arrangement. The partition arrangement is to divide the outer wall of the housing 1 into a number of areas, and each area is used for arranging one or more measuring components 3 of the same type. For example, taking the infrared switch 5 as a reference, the transparent portion 11 is divided equally into two sub-portions on the left and right, and each of the sub-portions can be arranged with one or more measuring components 3 of the same type. For example, after the transparent portion 11 is divided equally into two sub-portions on the left and right as shown in FIG. 11, a trypsin measuring component 36 is placed on the left sub-portion and an occult blood measuring component 34 is placed on the right sub-portion. The alternate arrangement is to divide the outer wall of the housing 1 into a number of areas, and each area is used for arranging one or more measuring components 3 of different types. Each type may include one or more measuring components 3. For example, taking the infrared switch 5 as a reference, the transparent portion 11 is divided into four sub-portions in a clockwise direction with 90° as a division interval, and each sub-portion can be arranged with multiple measuring components 3 of different types. For example, as shown in FIG. 12, the transparent portion 11 is equally divided with the infrared switch 5 as a reference into 4 sub-portions, i.e. [0, 90°], [90°, 180°], [180°, 270°], and [270°, 360°], in a clockwise direction. Each of the sub-portions is arranged with a trypsin measuring component 36 and a pepsin measuring component 35. The alternate arrangement applies to the environment where a relatively small volume of solution (liquid in gastrointestinal tract, for example) is present and only part of the housing 1 is immersed in the solution, to obtain a more complete detection result to the greatest extent and optimize the detection.

Further, in the embodiment as shown in FIGS. 6 to 8, the imaging assembly 4 comprises a lens 41 that is used to take images of the digestive tract and obtain color information of the measuring component 3. In this embodiment, the lens 41 can take the images of the measuring component 3. The images of the measuring component 3 and those of the digestive tract are transmitted together to an external receiver via the data transmission assembly 2. The external receiver can recognize the concentrations of the corresponding parameters to be measured and display them based on the images of the measuring component 3.

Figure 9:
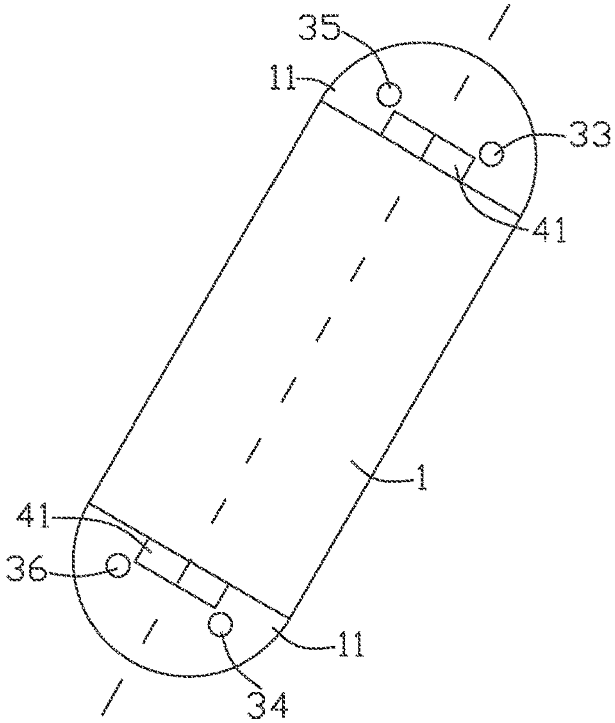
FIG. 9 is a schematic illustration of a fifth exemplar embodiment of the medical detection apparatus according to the aspects of the present invention.

As shown in FIG. 9, the medical detection apparatus may also comprise two imaging assemblies 4. Specifically, the housing 1 comprises a first end and a second end (upper shell 12 and lower shell 13) which are arranged opposite each other in the axial direction, and both the first end and the second end can have a transparent portion 11. The two imaging assemblies 4 are respectively arranged corresponding to the two transparent portions 11. The medical detection apparatus may be a dual-lens capsule endoscope.

Specifically, the measuring components 3 may be all mounted on the outer wall of the first end, or may be all mounted on the outer wall of the second end. At this point, an imaging assembly 4 of the medical detection apparatus is used to measure the concentration of the parameter to be measured, and the other is used to observe and take images.

Alternatively, in the medical detection apparatus, the outer wall of the first end of the housing 1 is arranged with a first measuring component, and the outer wall of the second end with a second measuring component. The first end may be provided with one or more the first measuring components, and the second end may be provided with one or more the second measuring components. The first measuring components and the second measuring components may be of the same or different types, and may have the same or different ranges. When the range is different, the medical detection apparatus can meet the need for detection of different concentration ranges at the same time.

In the embodiment shown in FIG. 9, the first end and the second end of the housing 1 are both provided with a lens 41, and the lens 41 is located in the transparent portion 11 of the first end and the second end. The first end may be provided with a pH measuring component 33 and a pepsin measuring component 35, and the second end may be provided with an occult blood measuring component 34 and a trypsin measuring component 36. Then, the first end of the medical detection apparatus, in addition to taking images of the digestive tract, can also measure the pH value and pepsin concentration in the digestive tract, and the second end of the medical detection apparatus, in addition to taking images of the digestive tract, can also measure the occult blood concentration and trypsin concentration in the digestive tract.

It should be noted that the medical detection apparatus may be a capsule endoscope, and also, it may be an image measuring device such as an electronic endoscope.

In an embodiment, when the medical detection apparatus is a capsule endoscope device, it comprises a capsule endoscope and at least one measuring component 3 affixed to the transparent portion 11 of the housing 1. The measuring component 3 may be of an annular structure, the inner diameter is 5 mm and the outer diameter is 6 mm, and the thickness is 40 um. In addition, diameters and thickness can also be other values. The body portion 31 of the measuring component 3 is affixed to the outer surface of the transparent portion 11 by medical UV glue (adhesive material 32). The measuring component 3 can be located between the effective imaging angle $\alpha$1 and the displayed image angle $\alpha$2, without affecting the normal display of images on a user interface, and the measurement result of the measuring component 3 can be observed through an external receiver.

In yet another embodiment, the capsule endoscope device comprises a capsule endoscope and a measuring component 3 affixed to the transparent portion 11 of the housing 1. The measuring component 3 may be strip-shaped, the length is 6 mm and the width is 2 mm, and the thickness is 5 um. In addition, the dimensions and thickness can also be other values. The body portion 31 of the measuring component 3 can be affixed onto the transparent portion 11 of the housing 1 by a medical adhesive (adhesive material 32), and the measuring component 3 can be within the effective imaging angle $\alpha$1.

Moreover, in an embodiment, the present invention provides a measuring component 3 of medical detection apparatus. The measuring component 3 comprises a polyionic gel and a dye, wherein the dye can be a substance having different colors according to the concentrations of the parameters to be measured, the polyionic gel is a solid substance formed by cross-linking polymerization of polymers, and the dye is filled in the polyionic gel. Due to a strong ionic interaction between the polyionic gel and the dye, the dye can be kept in the polyionic gel. The ions of the substance to be measured in the solution of an environment (digestive tract, for example) can pass through the polyionic gel and change color after combining with the dye, so as to display the concentration of the parameter to be measured in the solution.

The foregoing description of the embodiments of the invention has been presented for the purposes of illustration and description. It is not intended to be exhaustive or to limit the present invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the present invention.

What is claimed is:

1. A medical detection apparatus, comprising:

a housing; and a measuring component, mounted on the outer wall of the housing for measuring the concentration of a parameter to be measured in the external environment of the housing, wherein the measuring component comprises a polyionic gel and a dye, and the dye is filled in the polyionic gel through an ionic interaction between the polyionic gel and the dye; and the dye changes color when ions of the parameter to be measured pass through the polyionic gel and combine with the dye, such that the concentration of the parameter to be measured is different.

2. The apparatus of claim 1, wherein the measuring component comprises one or more of a pH measuring component, an occult blood measuring component, a pepsin measuring component, and a trypsin measuring component.

3. The apparatus of claim 2, wherein the dye of the pH measuring component is a pH sensitive dye which changes color in environments with different pH values.

4. The apparatus of claim 3, wherein hydrogen ions in the external environment of the housing enter the pH measuring component through the polyionic gel, and the hydrogen ions in the pH measuring component enter the external environment of the housing through the polyionic gel; and the pH-sensitive dye combines or dissociates with hydrogen ions to create a dynamic equilibrium.

5. The apparatus of claim 2, wherein the dye of the occult blood measuring component comprises a methylene blue dye which changes color in environments with different occult blood concentrations.

6. The apparatus of claim 5, wherein hemoglobin in the external environment of the housing combines and reacts with the polyionic gel and the methylene blue dye in the occult blood measuring component; and in the presence of hemoglobin, through a redox reaction, the methylene blue dye shows a color, and the methylene blue dye shows different colors when the concentration of the hemoglobin is different.

7. The apparatus of claim 2, wherein the dye of the pepsin measuring component comprises a bromophenol blue dye which changes color in environments with different pepsin concentrations.

8. The apparatus of claim 7, wherein the pepsin in the external environment of the housing combines with the polyionic gel and bromophenol blue dye in the pepsin measuring component; and the light scattering signal of the bromophenol blue dye changes to show different colors, and the color of the bromophenol blue dye is different when the concentration of pepsin is different.

9. The apparatus of claim 2, wherein the dye of the trypsin measuring component comprises a bromophenol purple dye which changes color in environments with different trypsin concentrations.

10. The apparatus of claim 9, wherein the trypsin in the external environment of the housing combines with the polyionic gel and bromophenol purple dye in the trypsin measuring component; and the volume and light scattering signal of the combined bromophenol purple dye change to show different colors, and the color of the bromophenol purple dye is different when the concentration of trypsin is different.

11. The apparatus of claim 2, wherein arrangement of the measuring components on the outer wall of the housing is a partition arrangement or an alternate arrangement.

12. The apparatus of claim 1, wherein the medical detection apparatus comprises a plurality of measuring components; and the ranges of the measuring components are not completely the same, or the resolutions of the measuring components are not completely the same.

13. The apparatus of claim 1, wherein the housing comprises a transparent portion; and the medical detection apparatus further comprises an imaging assembly, the imaging assembly is located in the inner cavity of the housing and observes the external environment of the housing through the transparent portion.

14. The apparatus of claim 13, wherein the housing comprises a first end and a second end which are arranged opposite each other in the axial direction, and both the first end and the second end comprise the transparent portion; and the medical detection apparatus comprises two imaging assemblies which are arranged corresponding to the two transparent portions;

wherein the measuring component is mounted on the outer wall of the first end or the second end; or, the medical detection apparatus comprises at least a first measuring component and a second measuring component, the first measuring component and the second measuring component have different ranges, one is mounted on the outer wall of the first end, and the other is mounted on the outer wall of the second end.

15. The apparatus of claim 13, wherein the medical detection apparatus further comprises a data transmission assembly;

the imaging assembly comprises a lens and an image sensor, the lens and the image sensor are connected by a mechanical structure or glue;

the image sensor is electrically connected or connected by signal to the data transmission assembly, and the lens is connected to the data transmission assembly by a mechanical structure or glue.

16. The apparatus of claim 15, wherein the lens is disposed in the inner cavity of the housing and has an effective imaging angle $\alpha\mathbf{1}$, and the transparent portion covers the space where the effective imaging angle $\alpha\mathbf{1}$ is located;

the image sensor has a display image angle $\alpha\mathbf{2}$, the transparent portion covers the space where the display image angle $\alpha\mathbf{2}$ is located, and $\alpha1>\alpha2$;

the measuring component is mounted on the outer wall of the housing and is located in the space between the effective imaging angle $\alpha\mathbf{1}$ and the display image angle $\alpha\mathbf{2}$;

the data transmission assembly obtains the data of the measuring component.

17. The apparatus of claim 15, wherein the lens is disposed in the inner cavity of the housing and has an effective imaging angle $\alpha\mathbf{1}$, and the transparent portion covers the space where the effective imaging angle $\alpha\mathbf{1}$ is located;

the image sensor has a display image angle $\alpha\mathbf{2}$, the transparent portion covers the space where the display image angle $\alpha\mathbf{2}$ is located, and $\alpha1>\alpha2$;

the measuring component is mounted on the outer wall of the housing and is located in the space that the display image angle $\alpha\mathbf{2}$ takes up; and the image sensor recognizes the data of the measuring component.

18. The apparatus of claim 17, wherein the measuring component is located in the middle of the space that the display image angle $\alpha\mathbf{2}$ takes up.

19. The apparatus of claim 1, wherein the measuring component is affixed to the outer wall of the housing by a transparent adhesive material.

20. The apparatus of claim 19, wherein the measuring component is further adhered to the outer wall of the housing by an edge sealant, and the edge sealant covers the outer edge of the measuring component.

21. The apparatus of claim 1, wherein the housing is a capsule-shaped structure; and the medical detection apparatus is a capsule endoscope.

22. A measuring component of a medical detection apparatus, comprising a polyionic gel, comprising an ion-exchange membrane structure, and a dye, the dye is filled in the polyionic gel through an ionic interaction between the polyionic gel and the dye; and the dye changes color when ions of the parameter to be measured pass through the polyionic gel and combine with the dye, such that the concentration of the parameter to be measured varies.

* * * * *